United States Patent [19]
Rose et al.

[11] Patent Number: 5,401,497
[45] Date of Patent: Mar. 28, 1995

[54] COMPOSITION FOR PERMANENT WAVING OF HUMAN HAIR AND USE OF AMMONIUM CARBAMATE IN SUCH COMPOSITIONS

[75] Inventors: Burkhard Rose, Darmstadt; Juergen Tennigkeit, Seeheim, both of Germany

[73] Assignee: Goldwell AG, Darmstadt, Germany

[21] Appl. No.: 853,997

[22] Filed: Mar. 19, 1992

[30] Foreign Application Priority Data

Mar. 22, 1991 [DE] Germany ............... 41 09 365.8

[51] Int. Cl.$^6$ ............................................. A61K 7/11
[52] U.S. Cl. ..................................................... 424/70.2
[58] Field of Search ..................... 424/70, 72, 71; 562/555; 574/477

[56] References Cited

U.S. PATENT DOCUMENTS

| | | | |
|---|---|---|---|
| 3,676,546 | 7/1972 | Ghilardi et al. | 424/71 |
| 4,025,444 | 5/1977 | Murphy et al. | 562/555 |
| 4,963,349 | 10/1990 | Mathews et al. | 424/72 |

FOREIGN PATENT DOCUMENTS 9100327  1/1991  WIPO .

OTHER PUBLICATIONS

Hawley's Condensed Chemical Dictionary–12th ed. p. 64.

*Primary Examiner*—Thurman K. Page
*Assistant Examiner*—Neil Levy
*Attorney, Agent, or Firm*—Birch, Stewart, Kolasch & Birch

[57] ABSTRACT

The invention is related to a composition for the permanent waving of human hair with improved properties of use, containing alkanediols in combination with ammonium carbamate as alkalinizing compound.

8 Claims, No Drawings

COMPOSITION FOR PERMANENT WAVING OF HUMAN HAIR AND USE OF AMMONIUM CARBAMATE IN SUCH COMPOSITIONS

This invention refers to a composition for permanent waving of human hair, i.e. a permanent waving composition with improved waving properties.

It is well known that a permanent waving procedure requires two working steps:

Reductive splitting of the cystine disulfide bonds of the hair by the action of a reducing agent, and subsequent neutralization by the application of an oxidizing agent whereby the cystine disulfide bonds are reinstated.

As already disclosed in the German pioneer patents 948 186 and 972 424, the conventional reducing composition used therefor is thioglycolic acid, e.g. as an ammonium or monoethanolamine salt, which has been partly replaced by glycerol monothioglycollate in recent years; however, thiolactic acid and its esters and inorganic sulfites, are also used.

Thereby, compositions that include thioglycollate have a pH value within the range of approx. 7.5 and approx. 9.0, especially within 8.5 to 9.0, whereby alkalinization is currently normally effected by the addition of ammonium(bi)carbonate (cf., e.g., U.S. Pat. No. 2,708,940.)

The reducing agent compositons often also include alkanediols or their ethers in a range from about 0.5 to about 35% by weight, preferably of about 1, particularly from about 2.5 to 15% by weight, which can also act as solvents and penetrating agents or as solubilizers or carriers. However, these compositions still require improvement with respect to their waving performance.

It has now been found that the curling effect of permanent waving compositions, i.e. their reducing phase, containing $C_3$–$C_6$-alkanediols and (or) their ethers, can be improved and the product efficiency is increased by adding ammonium carbamate of the formula

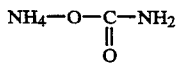

in a proportion of about 0.5 to about 10% by weight, preferably from 2 to 8% by weight, especially from 3 to 6% by weight, calculated to the total composition of the reducing composition.

Additionally, the composition according to this invention presents an improved smell during application.

The ammonium carbamate may be used on its own or in admixture with minor proportions of known alkalizing components, e.g. ammonia and ammonium carbonate or bicarbonate and monoethanolamine.

The reducing compositions are used as aqueous solutions, gels, emulsions (creams) or as aerosol foams, and may contain, in addition to reducing and alkalizing agents, hair conditioning substances such as cationic polymers, thickeners, so-called carriers to increase the penetration of a product, complexing agents, opacifiers, fragrances and also surface-active substances to improve wetting and penetration.

An essential component of the fixing or neutralizing compositions are oxidizers. The oxidizer used most commonly is hydrogen peroxide, the concentration of which is normally set between about 0.5 and about 5% by weight of the neutralizing composition.

Further oxidizers are alkali bromates, urea peroxide and sodium perborate, the two latter obviously in non-aqueous preparations.

These compositions are preferably packed as solutions or aerosol foams, rarely as gels.

The compositions include various other components such as stabilizers, plant extracts, hair conditioning ingredients and surfactants.

It has been mentioned that, as reducing agents in the permanent waving compositions of this invention, especially thioglycolic acid and ammonium thioglycollate, thiolactic acid, its salts and esters, cysteine and its hydrochloride, cysteamine, N-acetylcysteine, thioacetic acid, its salts and esters, and especially thioglycolic acid monoglycerol ester are used, besides of inorganic sulfites such as sodium bisulfite. When thioglycolic acid monoglycerol ester or a similar thioester is used, this composition is mixed with the remaining reducing composition immediately before application.

Depending on its structure, the concentration of the applied reducing agent normally ranges between about 1 and about 15% by weight of the reducing agent composition, preferably between about 3 and about 10% by weight.

The quantity of the alkalizing agent depends on the reducing agent. The reducing agent composition preferably contains from about 1 to about 10, particularly from about 2 to about 8% by weight of ammonium carbamate.

The proportion of ammonium carbamate obviously also depends on the fact, if and how many of further alkalizing agents such as ammonia and (or) ammonium(bi)carbonate are added. The pH value is recommended in the range from about 7 to about 8.5.

The permanent waving compositions of this invention preferably also contain surfactants. Their proportion is set from 0.1 to about 10, especially from about 1 to about 5% by weight.

The surfactants used in both, reducing compositions and in neutralizing compositions, are preferably the known anion-active agents which may also be used in combination With non-ionic surfactants.

Suitable anionic surfactants are especially the well known alkylether sulfates and carboxylic acids, particularly in the form of their alkali salts, as well as protein fatty acid condensates.

Suitable non-ionic surfactants are especially Chd 8–$C_{18}$-fatty alcohol polyglycol ethers, fatty acid polyglycol esters, fatty acid alkanolamide, amine oxides and particularly $C_8$–$C_{18}$-alkyl polyglycosides.

Amphoteric surfactants may also be used such as the well known betaines, and amido betaines as well as cation-active surfactants like quaternary ammonium compounds, particularly in cationic neutralizers.

An essential component of the compositions according to the invention is a $C_3$–$C_6$-alkanediol or its ether, especially mono-$C_1$–$C_3$-alkyl ether.

Preferred substances in this connection are 1,2-propanediol, 1,3-propanediol, 1-methoxypropanol(-2), 1-ethoxypropanol(-2), 1,3-butanediol, 1,4-butanediol, diethyleneglycol and its monomethylether and monoethylether, as well as dipropyleneglycol and its monomethylether and monoethylether.

The proportion of these diols is preferably set from about 1 to about 30, preferably from about 2.5 to about 15, most preferably from about 5 to about 10% by weight of the reducing agent composition.

In addition to the $C_3$–$C_6$-alkanediols or their ethers, also propylene carbonate (4-methyl-1,3-dioxolane-2-one), N-alkylpyrrolidone, glycerol and urea may be used.

The compositions according to the invention may of course include all those ingredients as are usual in permanent waving compositions; a detailed list of the same is omitted here.

To avoid repetition, reference is rather made to the state of technology, as described in "Ullmann's Encyclopedia of Industrial Chemistry", Vol. A12 (1986), pp. 588 to 591, as well as particularly the Monography of K. Schrader "Grundlagen und Rezepturen der Kosmetika", 2. Edition (1989, Hüthig Buch Verlag), pp. 823 to 840, and the survey of D. Hollenberg et al. in "Seifen-Öle-Fette-Wachse", 117 (1991), pp. 81 to 87.

The compositions and ingredients as disclosed therein are incorporated by reference; they may be also used within the scope of this invention.

The following examples shall illustrate the invention more closely.

EXAMPLE 1

| a) Reducing composition: | |
|---|---|
| Thioglycolic acid, 80% | 13.0% by wt. |
| Ammonium carbamate | 7.0 |
| Ammonia | 1.7 |
| $C_{12}$—$C_{14}$-Alkyl polyglycoside (condensation degree: 1.8) | 2.0 |
| 1,4-Butanediol | 3.5 |
| Perfume, Opacifier | q.s. |
| Water | @ 100.00 |
| b) Neutralizing composition: | |
| Hydrogen peroxide | 2.2% by wt. |
| Cationic polymer (e.g. Polymer JR) | 0.2 |
| $C_{12}$—$C_{14}$-fatty alcohol polyglycolether | 1.0 |
| Perfume, Stabilizer | q.s. |
| Water | @ 100.00 |

EXAMPLE 2

| a) Reducing composition: | |
|---|---|
| Thioglycolic acid, 80% | 10.0% by wt. |
| Ammonium carbamate | 6.0 |
| Ammonia | 1.1 |
| Cocoamido propyl betaine | 2.2 |
| 1,2-Propanediol | 5.0 |
| Perfume | q.s. |
| Water | @ 100.00 |
| b) Neutralizing composition: | |
| Hydrogen peroxide | 2.3% by wt. |
| Pentaoxyethyl stearyl ammonium chloride | 1.3 |
| $C_9$—$C_{11}$-Alkyl polyglycoside (condensation degree: 1.4) | 2.3 |
| Citric acid | 0.2 |
| Perfume, Acetanilide | q.s. |
| Water | @ 100.00 |

EXAMPLE 3

| a) Reducing composition: | |
|---|---|
| Thiolactic acid | 12.5% by wt. |
| Ammonia, 25% | 5.0 |
| Ammonium carbamate | 7.6 |
| Urea | 4.0 |
| Quaternary cationic polymer | 0.5 |
| Non-ionic fatty acid polyglycolester | 2.3 |
| Coco betaine | 0.8 |
| Dipropyleneglycol monomethyl ether | 3.5 |
| Opacifier, Perfume, Plant extract | q.s. |
| Water | @ 100.00 |
| b) Neutralizing composition: | |
| Hydrogen peroxide, 50% | 4.8% by wt. |
| Citric acid | 0.4 |
| Chamomile extract | 0.3 |
| $Na_2HPO_4$ | 0.4 |
| Sodium polyglycolether sulfate | 2.5 |
| Perfume, Stabilizer, Opacifier | q.s. |
| Water | @ 100.00 |
| Phosphoric acid to adjust pH to 3. | |

EXAMPLE 4

| a) Reducing composition | |
|---|---|
| Thioglycolic acid, 80% | 11.5% by wt. |
| Ammonium carbamate | 4.5 |
| Ammonium carbonate | 2.0 |
| $C_8$—$C_{12}$-alkyl polyglycoside (2.0) | 1.0 |
| Castor oil oxyethylate (40 EO) | 1.0 |
| 1-Methoxypropanol (—2) | 2.5 |
| Perfume | q.s. |
| Water | @ 100.00 |
| b) Neutralizing composition: | |
| Sodium bromate | 12.5% by wt. |
| Urea | 5.2 |
| Lauryldimethylamine oxide | 1.8 |
| Perfume, dyestuff, plant extract | q.s. |
| Water | @ 100.00 |

EXAMPLE 5

| a) Reducing agent: | |
|---|---|
| Ammonium thioglycollate | 5.0% by wt. |
| Cysteine | 2.5 |
| Ammonium carbamate | 3.8 |
| 1-Methoxypropanol (—2) | 5.2 |
| 1,3-Butanediol | 4.8 |
| Oleyl polyglycolether | 3.0 |
| Oleyl polyglycoside (condensation degree 1.8) | 0.2 |
| Perfume | q.s. |
| Water | @ 100.00 |
| b) Neutralizing composition: | |
| Hydrogen peroxide | 2.5% by wt. |
| Cetylstearyl alcohol | 2.0 |
| Sodium lauryl ether sulfate | 1.2 |
| $C_{12}$—$C_{16}$-Alkyl polyglycolether | 1.0 |
| Stabilizer, Perfume | q.s. |
| Water | @ 100.00 |

EXAMPLE 6

One portion of a composition A consisting of

60% by weight of glycerol monothioglycolic acid ester, 80% (glycerol residue),

15% by weight of glycerol mono-2-thiopropionic acid ester, 80% (glycerol residue), 25% by weight of 1,2-propanediol/dipropyleneglycol (weight proportion 2:1), is admixed to 2 parts of a composition B, adjusted to pH 7 with ammonia, held separately until application, consisting of 1.0% by weight of ammonium carbamate 0.3% by weight of protein hydrolyzate 1.5% by weight of $C_9$–$C_{11}$-alkyl polyglycoside (1.3)

0.5% by weight of castor oil polyglycol fatty acid ester 0.4% by weight of perfume oil
10.0% by weight of 1,2-propanediol
82.3% by weight of water,
and applied to the hair where it is left to process for 10 to 30 minutes.

After rinsing with water, neutralizing is effected with a composition C.

| Composition C: | |
|---|---|
| Hydrogen peroxide | 2.40% by wt. |
| Cationic polymer | 0.50 |
| Citric acid | 0.20 |
| Lauryl polyglycolether | 2.00 |
| Na$_2$HPO$_4$ | 0.20 |
| Phosphoric acid | 0.15 |
| Stabilizer | q.s. |
| Water | @ 100.00 |

The formula achieves shining, permanently waved hair without any irritation to the scalp.

EXAMPLE 7

| a) Reducing composition | |
|---|---|
| Thiolactic acid | 12.5% by wt. |
| Ammonia | 1.5 |
| Ammonium carbamate | 5.0 |
| Urea | 4.3 |
| Cationic polymer (e.g. polydimethyldiallyl ammonium chloride) | 0.5 |
| Non-ionic surfactant (fatty alcohol polyglycolether) | 1.0 |
| Dipropyleneglycol monomethyl ether | 5.0 |
| 1,2-Propanediol | 5.0 |
| Perfume | q.s. |
| Water | @ 100.00 |
| Neutralizing composition | |
| Hydrogen peroxide | 2.4% by wt. |
| Lauryldimethyl amine oxide | 2.0 |
| Citric acid | 0.3 |
| Protein hydrolyzate | 0.3 |
| Na$_2$HPO$_4$ | 0.4 |
| H$_3$PO$_4$ | 0.7 |
| Stabilizers, Perfume | q.s. |
| Water | @ 100.00 |

We claim:
1. A composition for the permanent waving of human hair, comprising:
   (A) at least one reducing component in an amount effective for the permanent waving of human hair,
   (B) an effective amount of at least one compound selected from the group consisting of C$_3$–C$_6$-alkanediols, ethers thereof, and mixtures thereof, and
   (C) 0.5 to 10% by weight of an alkalizing compound, wherein said alkalizing compound is ammonium carbamate, calculated based on the weight of the total composition.

2. The composition according to claim 1, wherein said composition contains 2 to 8% by weight ammonium carbamate, calculated based on the weight of the total composition.

3. The composition according to claim 1 or 2, wherein said composition contains 0.5 to 35% by weight of a compound selected from the group consisting of C$_3$–C$_6$-alkanediols, monoethers thereof, and mixtures thereof, calculated based on the weight of the total composition.

4. The composition according to claim 3, wherein said composition contains 1 to 15% by weight of a compound selected from the group consisting of C$_3$–C$_6$-alkanediols, monoethers thereof, and mixtures thereof, calculated based on the weight of the total composition.

5. The composition according to claim 1, wherein said composition contains a compound selected from the group consisting of 1,2-propanediol, 1-methoxypropanol(-2), a butanediol, and mixtures thereof.

6. The composition according to claim 1, wherein said composition contains 1 to 30% by weight 4-methyl-1,3-dioxolane-2-one, calculated based on the weight of the total composition.

7. A method for permanent waving of human hair which comprises applying to the hair an effective amount of a reducing composition comprising a permanent waving effective amount of a reducing component, an effective amount of at least one compound selected from the group consisting of C$_3$–C$_6$-alkanediols, ethers thereof, and mixtures thereof, and about 0.5 to about 10% by weight ammonium carbamate as an alkalinizing compound.

8. A composition for the permanent waving of human hair, consisting essentially of:
   (A) at least one reducing component in an amount effective for the permanent waving of human hair;
   (B) a carrier or penetrating agent comprising at least one compound selected from the group consisting of C$_3$–C$_6$-alkanediols, ethers thereof, and mixtures thereof,
   (C) 0.5 to 10% by weight of ammonium carbamate, calculated based on the weight of the total composition; and
   (D) water.

* * * * *